United States Patent
Davis

Patent Number: 5,928,190
Date of Patent: Jul. 27, 1999

[54] SINUS VACUUM FLUSH

[75] Inventor: Shirley Davis, P.O. Box 801, Whitefish, Mont. 59937

[73] Assignee: Shirley Davis, Whitefish, Mont.

[21] Appl. No.: 08/910,206

[22] Filed: Aug. 13, 1997

[51] Int. Cl.$^6$ .................................................. A61M 11/00
[52] U.S. Cl. ............................................. 604/94; 604/39
[58] Field of Search ................................. 604/35, 39, 73, 604/94, 118, 173, 149, 318, 319

[56] References Cited

U.S. PATENT DOCUMENTS

| | | | |
|---|---|---|---|
| D. 308,100 | 5/1990 | Bishop . | |
| 2,566,806 | 4/1951 | Miller | 604/94 X |
| 3,847,145 | 11/1974 | Grossan . | |
| 4,029,095 | 6/1977 | Pena | 604/94 X |
| 4,403,611 | 9/1983 | Babbitt et al. | 604/94 X |
| 5,098,386 | 3/1992 | Smith . | |
| 5,114,415 | 5/1992 | Shedlock | 604/94 X |
| 5,381,548 | 1/1995 | Filshie . | |

*Primary Examiner*—Ronald Stright
*Assistant Examiner*—A. T. Nguyen

[57] ABSTRACT

A duel system for flushing and vacuuming the sinuses comprising a main plate (1) having two voids (42 and 43) with collars (44 and 45) extending below. The voids hold two containers (25 and 26) with lids (9 and 10). Wing clips (2) attached to the main plate (1) holds adjuster plate (5) in recess (32) having mortise (33) within. Adjuster plate (5) accepts suction tube (39) and saline tube (40), with nose plugs (7E and 7F) on their ends. Wing clips (2) when rotated, allows adjuster plate (5) to be picked up and rotated, reversing tubes (39 and 40) and nose plugs (7E and 7F). Tubes (38, 39, 40 and 41) are secured in slots (27, 28, 29 and 30). Air compressor (24) creates pressure in pressure container (26) through pressure tube (41). The pressure pushes saline through saline tube (40) that passes up through lid (10), mortise (33), hole (6) in adjuster plate (5), and has nose plug (7F) on the end. Saline passes through nose plug (7F), up one nostril through the sinuses and down the other nostril. Saline enters nose plug (7E) on the end of suction tube (39) which passes down through hole (6) in adjuster plate (5), mortise (33), and through vacuum lid (9). Saline is drawn through nose plug (7E), suction tube (39), and into vacuum container (25). Congestion is also drawn along with the saline. The vacuum is initiated when valve (12) is covered. Vacuum lid (9) is connected to vacuum attachment (21) with vacuum tube (38). Vacuum attachment (21) controls the amount of suction. Tube (38) communicates with a conventional vacuum cleaner hose (34), or vacuum pump (8). The systems can be used separately or together.

16 Claims, 8 Drawing Sheets

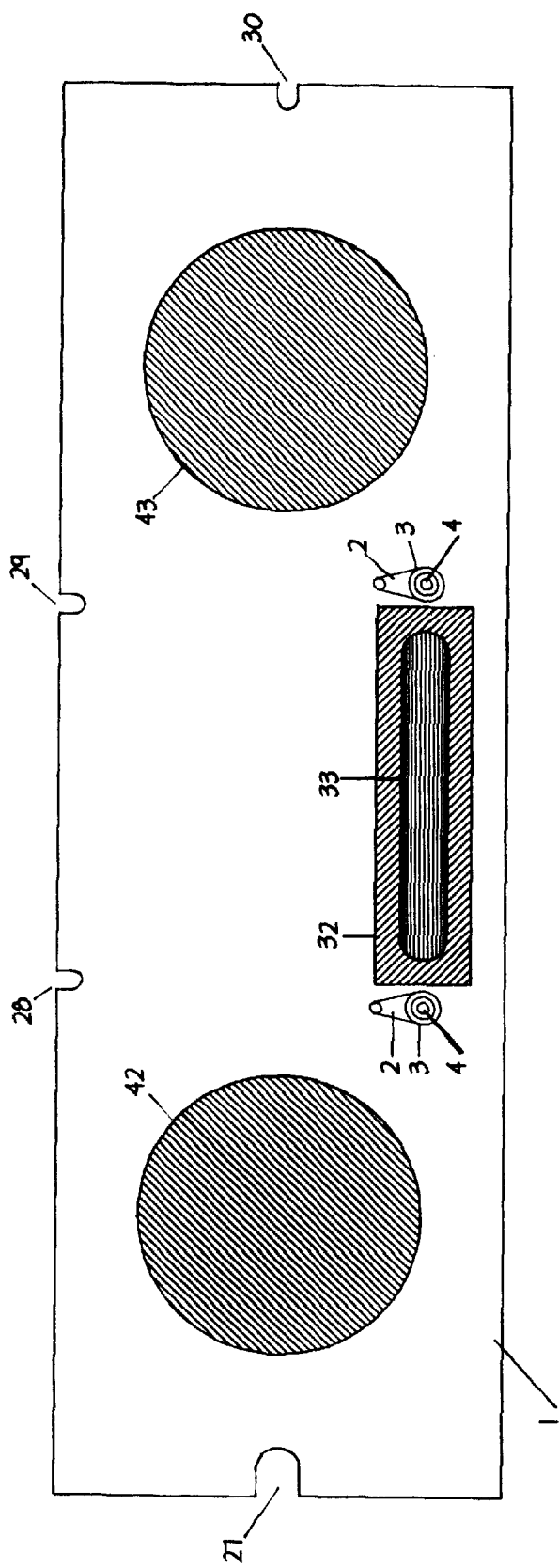

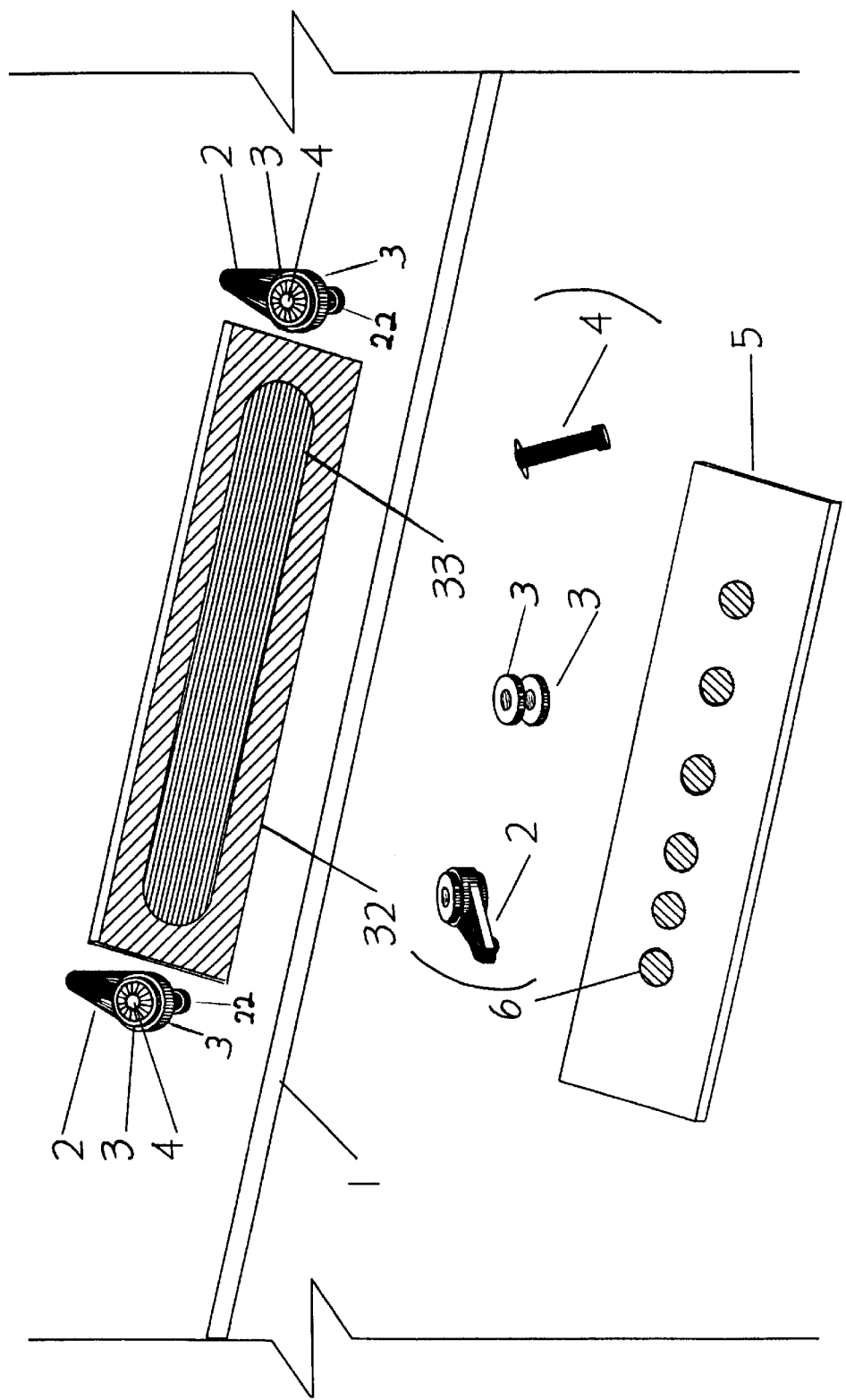

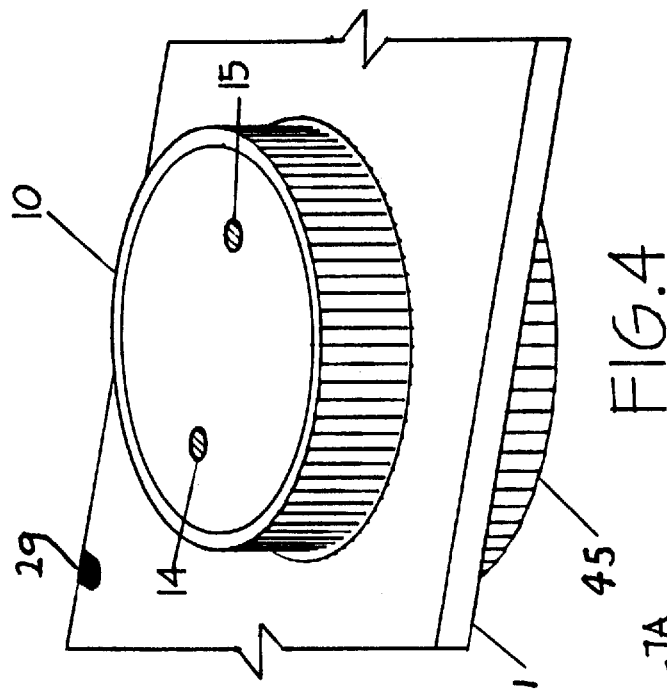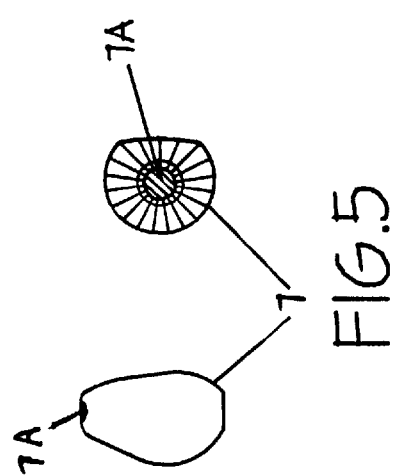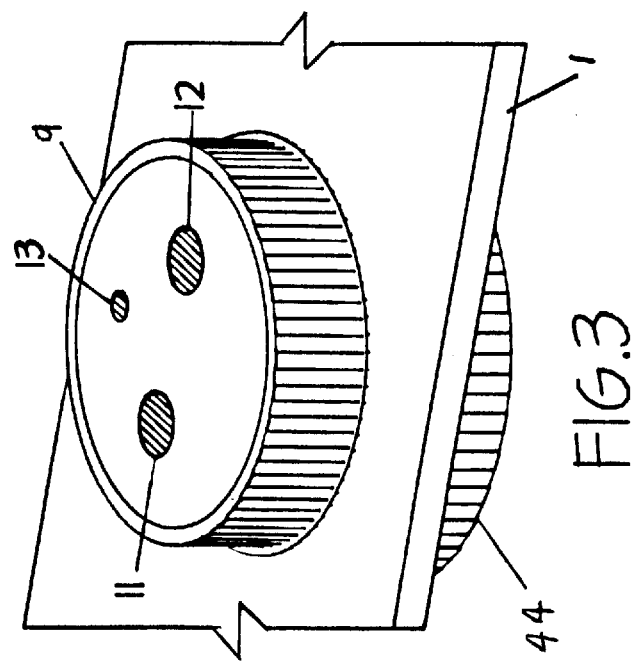

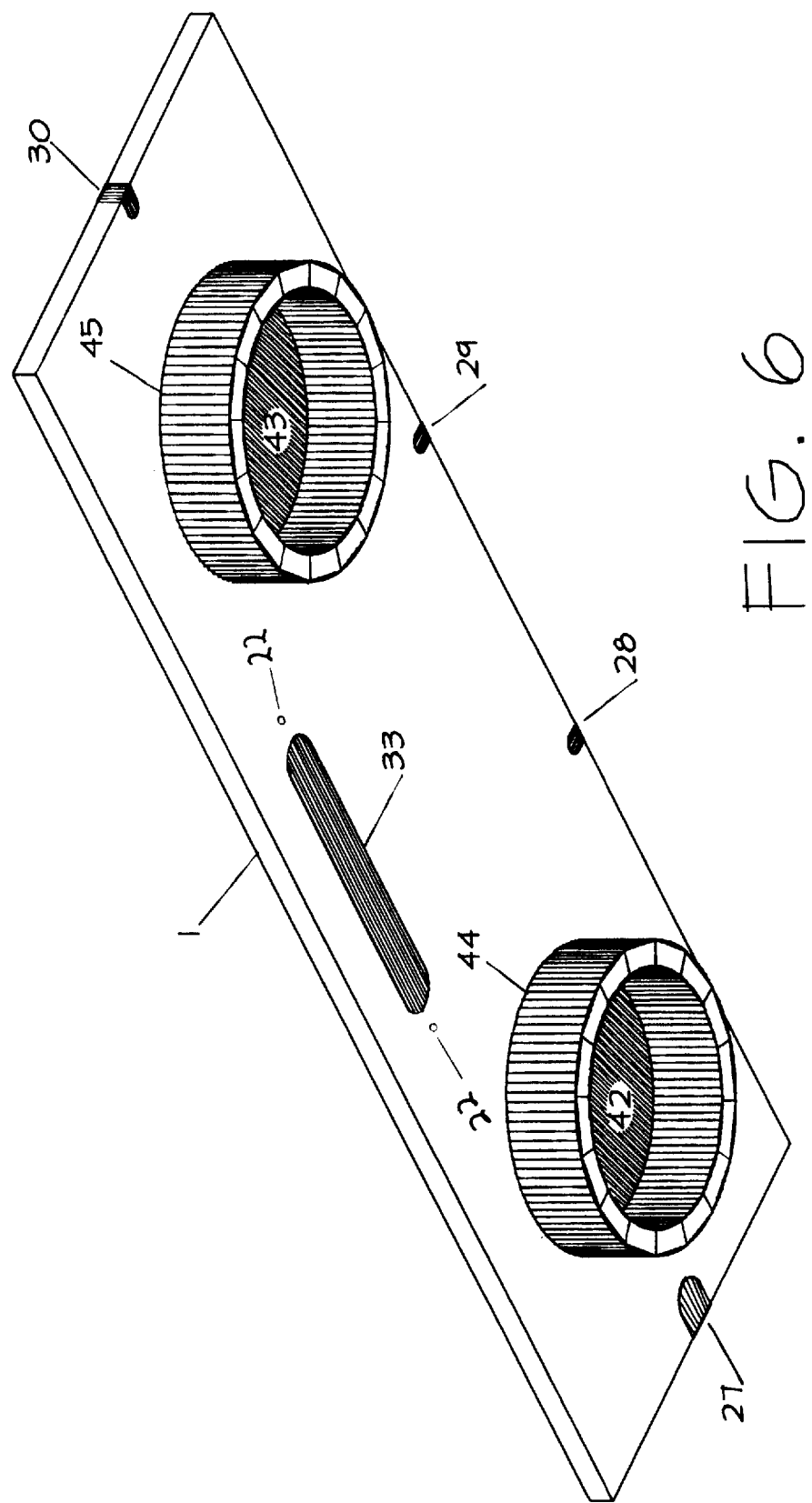

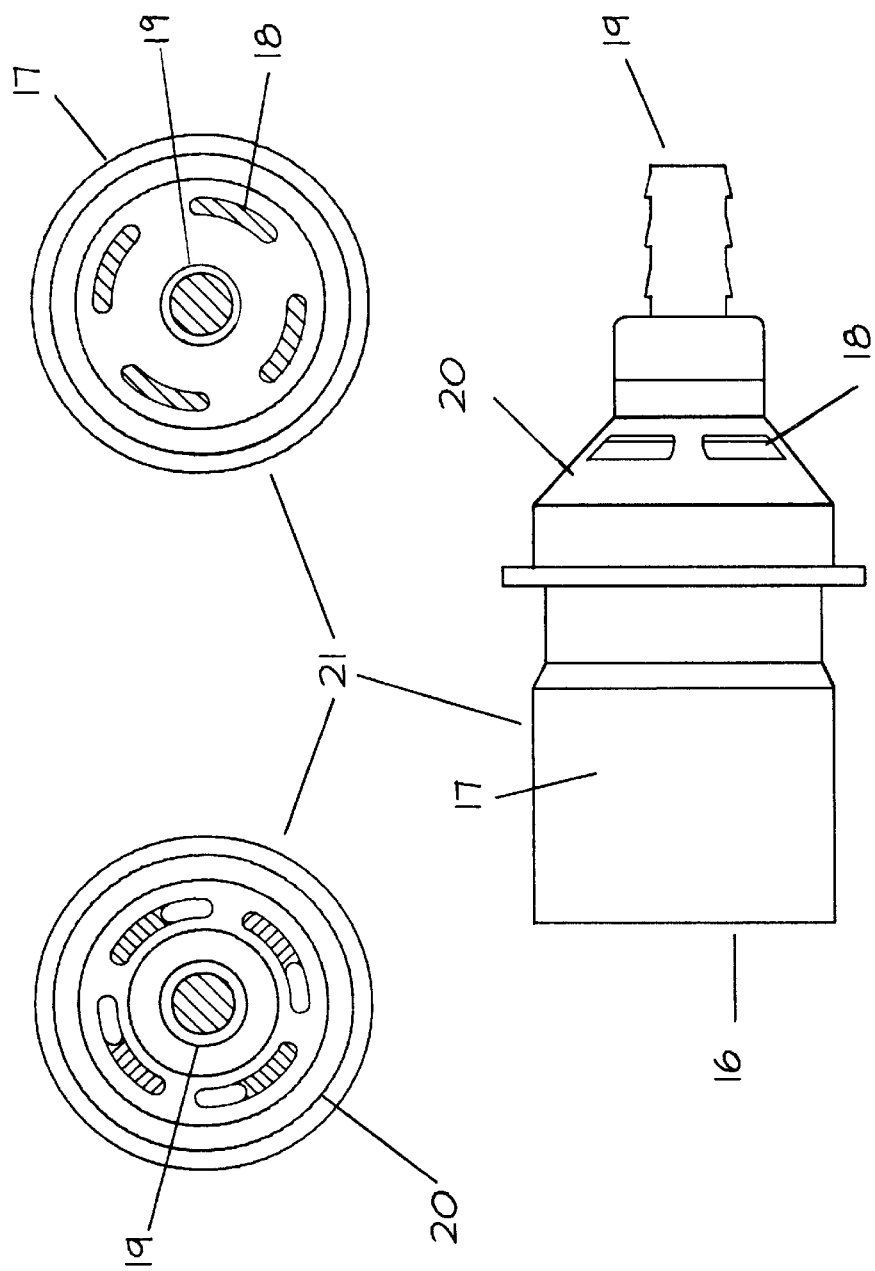

SINUS VACUUM FLUSH

CROSS-REFERENCE TO RELATED APPLICATIONS

Not applicable

STATEMENT REGARDING FEDERALLY SPONSORED RESEARCH OR DEVELOPMENT

Not applicable

REFERENCE TO A MICROFICHE APPENDIX

Not applicable

FIELD OF INVENTION

This invention relates to an apparatus which flushes and vacuums mucus from nasal and sinus cavities. More specifically, the invention relates to a portable flushing vacuum system to deliver medication and withdraw material from the sinuses without irritating the nasal tissue.

BACKGROUND OF THE INVENTION

The maxillary sinus has a poor drainage system that requires the ciliary transport system to work against gravity. Ciliary activity is slowed or stopped by alterations in temperature, bacterial toxins and other factors such as changes in the pH. The maxillary sinus becomes infected very easily and is the most difficult to clear. All of the other paranasal sinuses are capable of gravity drainage. The maxillary sinus opening however is located high in the nasal sinus above the level of the middle turbinate. Consequently, the maxillary sinus does not cleanse well.

Increased mucus concentration causes a congestion in the nostrils, sinus cavities and ears leading to painful headaches. Sinus fluids which drain by gravity tend to cause irritation of the throat. When excessive mucus is produced because of infection or weather conditions there is much discomfort, thereby affecting a person's daily performance.

BACKGROUND PRIOR ART

There are various prior art devices constituting attempts to provide a portable and efficiently operating sinus cavity aspiration device. The U.S. Pat. No. 3,833,001 Abrahams September 1974 discloses a portable de-mucosant which requires large amounts of water to operate a venturi tube for creating the necessary suction to drain the nasal and maxillary sinuses. Thus, this prior art device is dependent upon the use of large amounts of water.

U.S. Pat. No. 4,403,611 Babbitt September 1983 discloses a portable evacuator that produces its own vacuum to withdraw mucus from the sinus cavities. Thus, this prior art device is dependent upon the use of suction only.

U.S. Pat. No. 5,114,415 Shedlock May 1992 is a power driven suction device with a tube and nozzle to be placed in the nostril. This device relies on suction only. Thus the three prior art devices are sufficient and are necessarily dependent upon the use of suction only.

U.S. Pat. No. 4,029,095 Pena June 1977 is a device for circulating treating fluid through the nasal sinuses. It has a suction inlet and a pressure outlet with an electric pump in-between. The fluid leaves the pressure chamber and is forced up one nostril and down the other, where it enters the suction chamber. It is then sucked through a filter and the pump and then re-circulated through the sinuses again. It would have to be used with some sort of disinfectant to kill bacteria or it could contaminate all sinus cavities. This would also kill the good bacteria that keep the harmful bacteria under control. The use of saline is common to rinse the sinuses. If it were used in this device it could spread the infection to all sinus cavities. Although this device does use pressure and suction the use of this device could be very unsanitary.

U.S. Pat. No. 2,566,806 Miller September 1951 is an atomizer bulb type device. It has two glass bulbs. One to retain waste fluids and has two appendages for insertion into both nasal openings. The other glass bulb has fluid that is atomized and blow into the nostrils using pressure from a hand operated flexible bulb connected to the glass bulb. Another hand operated flexible bulb connected to the same glass bulb, has a valve to release pressure when compressed. When released the bulb creates a suction drawing fluid from the nostrils. This item should be effective but looks very cumbersome. The device blows pressure up both nostrils at the same time and the suction is in both nostrils at the same time. There would be a lack of circulation and could build unwanted pressure in the ears. There is also the possibility of breakage with the thin glass bulbs. However the device does use both suction and pressure.

U.S. Pat. No. 5,318,548 Filshie June 1994 is a hand operated pump extractor with a mucus compartment. The main use for this device is for new born babies. U.S. Pat. No. 5,098,386 Smith March 1992 is also for infants. These devices also depend on suction only.

U.S. Pat. No. 4,964,850 Bouton et al October 1990 is a sinus aerator only, and is surgically implanted. U.S. Pat. Nos. 4,737,141 Spits April 1988 and 5,139,502 Berg February 1990 are sinus drain tubes. Both are also surgically implanted at great cost and discomfort.

Other prior art devices shown in U.S. Pat. Nos. 1,481,008 Hodlick January 1924, 1,766,668 Miller, 2,078,180 Kronenberg April 1937, 2,280,992 Wright et al April 1942, 2,879,768 Anderson March 1959 and 3,502,078 Hill et al March 1970 include flexible bulb type devices to provide intermittent vacuum pulses to relieve the mucus. These are generally inefficient and unsanitary.

U.S. Pat. No. 5,433,343 Meshberg July 1995 is a delivery system for measured quantities of liquids. The device is mainly for dispensing medications into the nostril.

Attempts to solve the problems associated with congestion include surgically implanted drain tubes, medication, flushing, and evacuator devices. Medication generally gives only temporary relief at significantly high cost and sometimes with various side effects. Known evacuator devices are operated only in physician's offices where treatment requires not only time, but also a significantly large medical bill. While the known evacuator devices are reliable and efficient, their use is inconvenient, expensive and most rely on suction only.

PURPOSE OF THE INVENTION

The primary object of the Sinus Vacuum Flush is to provide a portable, flushing vacuum apparatus which may be used at home to effect the flushing and evacuation of the nasal passages and maxillary sinuses without damage to the nasal tissues.

Another object of the invention is to provide a flushing vacuum system for aspirating saline and mucus material from the nasal and sinus cavities while providing an apparatus that can be fully sterilized.

Another object of the invention is to provide an efficient portable, flushing vacuum apparatus which provides an intermittent or continuous fluid pressure with an intermittent, variable continuous suction. Thus, making it available for periodic use to keep nasal and sinus cavities clear of mucus material. In addition the pressure system and vacuum system can be operated independent of each other.

Another object of the invention is to provide an apparatus that has an adjuster plate and nose plugs which can be used separate from the main plate. Thus, allowing the nose plugs to be inserted into the nostrils while holding the adjuster plate. The head can then be tilted forward, down, and from side to side allowing the maxillary sinus to be cleansed more thoroughly. Reversing the adjuster plate, which reverses the nose plugs, allows the suction and pressurized fluid to be placed in the opposite nostrils cleansing and vacuuming the sinuses on the opposing side.

A still further object of the invention is to provide a portable, flushing vacuum apparatus to deliver a pressurized liquid medication or saline and hydrogen peroxide into the sinus cavities. This destroys bacteria and relieves sinus infection while avoiding the use of antibiotics. It also delivers a pressurized liquid containing friendly bacteria, thus preventing the re-growth of harmful bacteria. The use of this device at the first sign of a cold can sometimes prevent its onset. Prior art used flushing of the sinuses or evacuator devices, but few use both at the same time. Surgery is also used frequently to implant aerators or drain tubes in the sinus cavities. With today's continuing air pollution, this device can be very beneficial in preventing and treating sinus infections and relieving the symptoms of allergies, colds, and flu.

BRIEF DESCRIPTION OF THE SEVERAL VIEWS OF THE DRAWING

FIG. 1 Is a main plate 1, a void 42, a void 43, and four retainer slots 27, 28, 29, and 30, a recess 32 with a mortise 33 and wing clips 2.

FIG. 2 Is an adjuster plate 5 with holes 6, recess 32, mortise 33, and wing clips 2, with washers and rivet.

FIG. 3 Is a vacuum lid 9, hole 11, regulator valve 12, hole 13, collar 44 and partial view of the main plate 1.

FIG. 4 Is a pressure lid 10, hole 14, hole 15, collar 45 and partial view of the main plate 1.

FIG. 5 Is a nose plug 7 and orifice 7-A.

FIG. 6 Is the reverse side of the main plate 1, collar 44, collar 45, void 42, void 43, mortise 33, and retainer slots 27, 28, 29, 30 and rivet holes 22.

FIG. 7 Is a vacuum attachment 21 with an end view of a mid section 17 with a tip 19, suction regulator holes 18, and suction adjuster sleeve 20.

LIST OF REFERENCE NUMERALS

Figure 8:
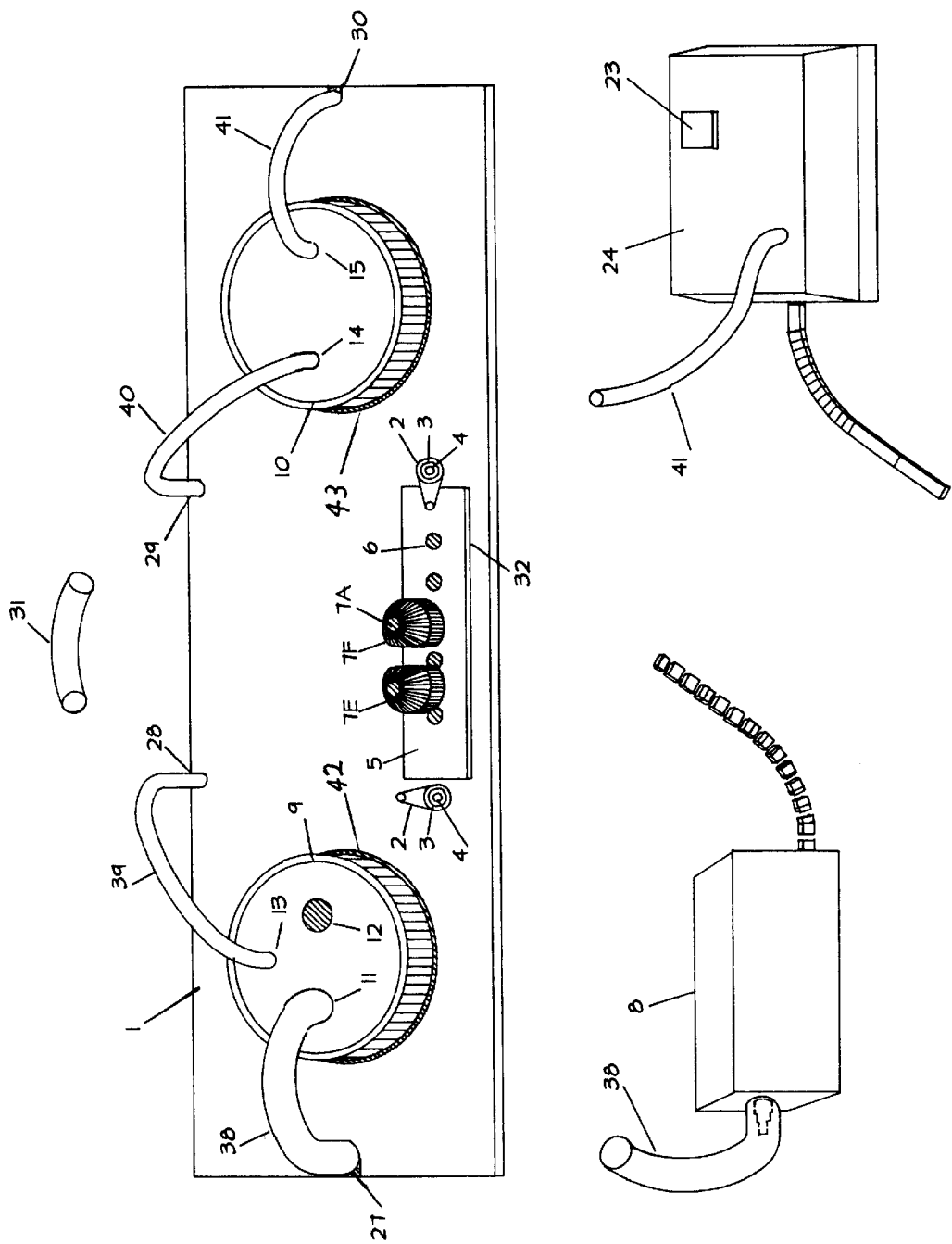
FIG. 8 Shows how everything fits in place when the vacuum lid 9 with valve hole 12, tube holes 11 and 13, pressure lid 10 with tube holes 14 and 15 are in place. The adjuster plate 5 is in the recess 32, wing clips 2 and nose plugs 7-E and 7-F are in position. It also shows transport tubes 38, 39, 40 and 41 in the retainer slots 27, 28, 29 and 30. It shows a small air compressor 24 with off-on switch 23. Also shown is a flushing tube 31, and a vacuum pump 8.

1. Main plate—plastic (0.64 cm×12.07 cm×38.1 cm) (¼"×4¾"×15") (rectangle horizontal slab)

2. Wing clips—plastic (rotatably mounted keepers)

3. washers

4. Rivets

5. Adjuster plate—plastic (0.32 cm×2.54 cm×10.16 cm) (⅛"×1"×4") (rectangle adjuster means)

6. Holes—in adjuster plate (5) (0.6 cm) (¹⁵⁄₆₄") (plurality of holes)

7. Nose plug—plastic (nasal seal)

7-A. Orifice—in nose plug (7)

8. Vacuum pump—(commercially obtained) (means for creating a vacuum)

9. Vacuum lid—plastic (tight sealing closure)

10. pressure lid—plastic (tight sealing closure)

11. Hole—for vacuum tube (38) (lid 9) (1.2 cm) (¹⁵⁄₃₂") (hole means)

12. Regulator valve—(lid 9) (1.2 cm) (¹⁵⁄₃₂") (valve means)

13. Hole—for suction tube (39) (lid 9) (0.56 cm) (⁷⁄₃₂") (hole means)

14. Hole—for saline tube (40) (lid 10) (0.56 cm) (⁷⁄₃₂") (hole means)

15. Hole—for pressure tube (41) (lid 10) (0.56 cm) (⁷⁄₃₂") (hole means)

16. Opening—of vacuum attachment (21) (4.92 cm) (1¹⁵⁄₁₆") diameter opening

17. Mid section—of vacuum attachment (21)—plastic

18. Suction regulator holes—in vacuum attachment (21)

19. Tip—of vacuum attachment (21)—plastic—tip accepts flexible tube (38)

20. Suction adjuster sleeve—of vacuum attachment (21)—plastic

21. Vacuum attachment—plastic (commercially obtained)

22. Holes—for rivets (0.32 cm) (⅛")

23. Off-On switch—for air compressor—plastic (commercially obtained)

24. Air compressor—such as used for aquariums (commercially obtained) (means for creating pressure)

25. Vacuum Jar—glass (vacuum container)

26. Pressure jar—glass (pressure container)

27. Retainer slot—for vacuum tube (38) (1.2 cm) (¹⁵⁄₃₂")

28. Retainer slot—for suction tube (39) (0.56 cm) (⁷⁄₃₂")

29. Retainer slot—for saline tube (40) (0.56 cm) (⁷⁄₃₂")

30. Retainer slot—for pressure tube (41) (0.56 cm) (⁷⁄₃₂")

31. Flushing tube—(0.95 cm×7.62 cm) (⅜"×3" long) (flexible hollow transport means)

32. Recess—(0.32 cm×3.18 cm×10.8 cm) (⅛" deep× 1¼"×4¼") accepts adjuster plate (5)

33. Mortise—(1.27 cm×8.89 cm) (½"×3½") in center of recess (32) for tubes (39 and 40)

34. Conventional vacuum cleaner—hose (commercially obtained) (Means for creating a vacuum)

35. Side vents—in vacuum tube (38) (vent holes)

36. End plug—in vacuum tube—(38) plastic (end seal)

37. Drip tray—between jars 25 and 26—plastic (commercially obtained)

38. Vacuum tube—flexible tubing (1.27 cm×0.95 cm×1.82 m) (½" OD×⅜" ID×6') (flexible hollow transport means)

39. Suction tube—flexible tubing (0.64 cm×76.2 cm) (¼"×30") (flexible hollow transport means)

40. Saline tube—flexible tubing (0.64 cm×76.2 cm) (¼"×30") (flexible hollow transport means)

41. Pressure tube—flexible tubing (0.64 cm×50.8 cm) (¼"×20") (flexible hollow transport means)

42. Hole—for vacuum jar (25) (7.46 cm) (2¹⁵⁄₁₆") (large void)

43. Hole—for pressure jar (26) (7.46 cm) (2¹⁵⁄₁₆") (large void)

44. Collar—beneath vacuum jar hole (42)—plastic (0.64 cm×7.46 cm) (¼" wall×2¹⁵⁄₁₆" diameter)

45. Collar—beneath pressure jar hole (43)—plastic (0.64 cm×7.46 cm) (¼" wall×2¹⁵⁄₁₆" diameter)

SUMMARY OF THE INVENTION

The Sinus Vacuum Flush apparatus as disclosed herein comprises a rectangle main plate with two large holes. Each hole having a collar extending below the main plate, to rest on the shoulders of a vacuum container, and a pressure container that fit therein. The main plate has four slots on its edges to stabilize four flexible tubes. The four flexible tubes are, a vacuum tube connecting a vacuum attachment to a vacuum lid. A suction tube connecting the vacuum lid to a nose plug. A pressure tube connecting an air compressor to a pressure lid. A saline tube connecting the pressure lid to an opposing nose plug.

The main plate has a rectangle recess with a mortise located therein, to accept a rectangle adjuster plate, that accepts the flexible suction tube and saline tube. Two wing clips rotatably mounted on the main plate at each end of the recess, secure the rectangle adjuster plate in the recess. The wing clips are secured in two holes in the main plate with washers and rivets.

The pressure container has a tight sealing lid with two holes. A hole accepts the flexible pressure tube from the small air compressor with an off-on switch. A second hole accepts the saline tube that passes up through the mortise in the main plate and adjuster plate to the nose plug mounted on the tube end for insertion into a nasal opening.

The vacuum container has a tight sealing lid with three holes. A hole accepts the flexible vacuum tube from the vacuum attachment or a vacuum pump. On the under side of the lid, the vacuum tube has two vent holes in its sides and a plug in its end. This prevents fluid from being drawn into the vacuum tube. A second hole is a regulator valve and is to be covered with a finger, thereby starting the vacuum in the container. The vacuum can be stopped and started in this manner. A third hole accepts the flexible suction tube that passes up through the mortise in the main plate and adjuster plate to the nasal seal mounted on the tube end for insertion into an opposing nasal opening.

The vacuum attachment has an opening suitable to fit a conventional vacuum cleaner hose. The attachment's mid section has suction regulator holes that are partially covered by a rotating suction adjuster sleeve. This regulates the amount of suction to the vacuum container. The tip of the mid section accepts the vacuum tube coming from the vacuum lid.

The Sinus Vacuum Flush Apparatus provides a vacuum container to allow fluid to be drawn from the sinuses through a nose plug and flexible suction tube and collected in the container, while preventing mucus from entering the vacuum tube. The double container system also comprises a pressure container to deliver saline and medication to rinse the sinus cavities. The pressurized fluid system and vacuum system can be operated separately or together.

The nose plugs are large on one end and small on the opposing end. They are reversible to adjust to different sizes of nasal openings. The nose plugs can be removed from the tube ends and placed in the pressure container. The container having hydrogen peroxide to disinfect the nose plugs and system. The vacuum container should be emptied, rinsed and recapped. The saline tube and the suction tube should be removed from the holes in the adjuster plate and mortise and connected together with a flushing tube. The air compressor and vacuum should be turned on. A finger placed over the regulator valve will draw the fluid through the system disinfecting the tubes. The remainder of the system can be washed with soap and water. The containers can be put in a dishwasher for sterilization.

This device can be used to prevent colds and sinus infections as well as alleviate allergy symptoms.

DETAILED DESCRIPTION OF THE INVENTION

FIG. 1 a top view of a (0.64 cm×12.07 cm×38.1 cm) ¼"×4¾"×15" slab of rigid polyethylene plastic known as the main plate 1. Two inches in from each end are two (7.46 cm) 2¹⁵⁄₁₆" holes. Hole 42 is for the vacuum container 25. Hole 43 is for the pressure container 26. Two plastic collars 44 and 45 (0.64 cm wall×7.46 cm) ¼" wall×2¹⁵⁄₁₆" diameter (not seen in drawing) are mounted to the main plate beneath each large hole, to make the hole depth (2.22 cm) ⅞", to rest upon containers 25 and 26 shoulders. Collar 44 corresponds with hole 42. Collar 45 corresponds with hole 43 (See FIG. 6). In the center front portion of the main plate 1 there is a rectangle recess 32 (0.32 cm×3.18 cm×10.8 cm) 1/8 ×1¼"× 4¼". It is ⅛" deep to accommodate the adjuster plate 5 (not seen in drawing). There is a mortise 33 (1.27 cm×8.89 cm) ½"×3½" within the center of the recess 32. On each end of the recess 32 there are two wing clips 2 held in place by washers 3 and rivets 4 in two holes 22 (not seen in drawing) in the main plate 1 (see FIG. 2). The wing clips 2 hold the adjuster plate 5 in place in the recess 32 on the main plate 1. The mortise allows for two (0.64 cm) ¼" flexible hollow transport tubes 39 and 40 to pass up through the mortise 33 and adjuster plate 5. Around the edges of the main plate 1 are four retainer slots. Slot 27 is (1.2 cm) ¹⁵⁄₃₂". Slots 28, 29 and 30 are (0.56 cm) ⁷⁄₃₂". Vacuum tube 38 is (1.27 cm OD×0.95 cm ID×1.82 m) ½" OD×⅜" ID×6 foot and fits in slot 27. Tubes 39 and 40 are (0.64 cm×76.2 cm) ¼"×30". Suction tube 39 fits in slot 28. Saline tube 40 fits in slot 29. Pressure tube 41 is (0.64 cm×50.8 cm) ¼"×20" and fits in slot 30 (tubes not shown in drawing) (See FIG. 8).

FIG. 2 a top view of a rectangle adjuster plate 5 is a (0.32 cm×2.45 cm×10.16 cm) ⅛"×1"×4" piece of rigid plastic with six (0.06 cm) ¹⁵⁄₆₄" holes 6. The six holes are drilled at different measurements apart to adjust distance between the flexible suction tube 39 and the saline tube 40, thereby adjusting the distance between the two nose plugs 7E and 7F on the tube endings (not shown in drawing). An exploded view of the rectangle recess 32 with a mortise 33 within the center is shown. (It is described in FIG. 1). The wing clip 2, washers and rivet are shown in detail. (They are described in FIG. 1).

FIG. 3 a top view of a plastic vacuum lid 9 to the vacuum container 25 has three holes 11, 12 and 13. Hole 11 (1.2 cm) ¹⁵⁄₃₂" is for the flexible vacuum tube 38 from the vacuum attachment 21 or a commercially obtained vacuum pump 8. Regulator valve 12 (1.2 cm) 15/32" when covered will start the vacuum in container 25. Hole 13 (0.56 cm) ⁷⁄₃₂" accepts the flexible suction tube 39 with the nose plug 7-E on the opposing end.

FIG. 4 a top view of a plastic pressure lid 10 to the pressure container 26 has two holes 14 and 15. Hole 14 (0.56 cm) 7/32 accepts the flexible saline tube 40 with the nose plug 7-F on its opposing end. Hole 15 (0.56 cm) 7/32 accepts the flexible pressure tube 41 that comes from a small commercially obtained air compressor 24 with an off-on switch 23.

FIG. 5 a side view, and top view of a plastic nose plug 7. The nose plug has a center orifice 7-A. The nose plug is large on one end and small on the opposing end. It is reversible to accommodate different sized nasal openings.

FIG. 6 a bottom view of the main plate 1 with the mortise 33, rivet holes 22 and the collars 44 and 45. The collars extend below holes 42 and 43 to rest on the shoulders of containers 25 and 26. (The collars are described in FIG. 1). The retainer slots 27,28,29,and 30 are seen.

FIG. 7 a side view of a commercially obtained plastic vacuum attachment 21. The opening 16 of the attachment is (4.92 cm) 1 5/16" to fit a conventional vacuum cleaner hose 34. The mid section 17 has a sleeve 20 that rotates to open or partially restrict the suction regulator holes 18. The end view shows suction regulator holes 18 restricted. The sleeve 20 rotates to align the slots with the holes 18, adjusting the amount of suction from the vacuum cleaner. The tip 19 accepts (0.95 cm×1.27 cm) 3/8" ID×1/2" OD flexible tubing 38 from the vacuum lid 9.

FIG. 8 a top view of the main plate 1 with lids 9 and 10 in place in holes 42 and 43 in the main plate 1. Tubes 38, 39, 40 and 41 are in retainer slots 27, 28, 29 and 30. The adjuster plate 5 is locked in place in the recess 32 by wing clips 2. The suction tube 39 and saline tube 40 are through the holes 6 in the adjuster plate 5. The suction tube 39 is connected to the nose plug 7-E. The saline tube 40 is connected to the nose plug 7-F. The nose plug orifice 7-A is seen. The electric air compressor 24 with an off-on switch 23, a commercially obtained vacuum pump 8, and flushing tube 31 are shown.

OPERATION FIG. 9 AND FIG. 10

Figure 9:
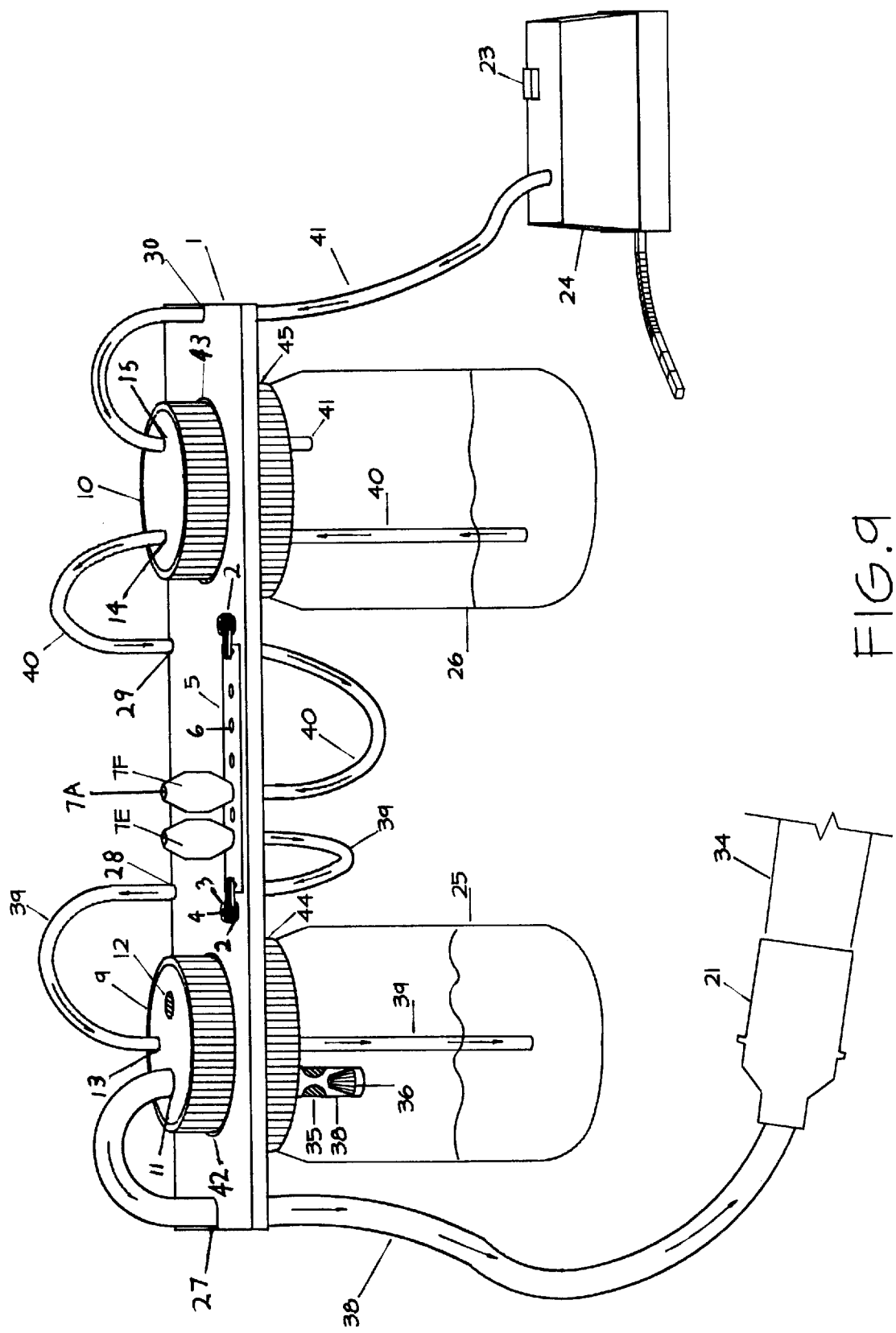
FIG. 9 Is the complete Sinus Vacuum Flush system ready for operation.

FIG. 9 a side view of the complete Sinus Vacuum Flush. The vacuum container 25 and pressure container 26 are in holes 42 and 43 of the main plate 1. Pressure container 26 is filled no more then 1/2 full of saline. The air compressor 24 pushes air through the pressure tube 41 into the pressure container 26. The pressure in container 26 pushes saline up through the saline tube 40 and through the nose plug 7-F. The saline is gently forced up one nostril, through the sinuses and down the other nostril. The liquid then enters nose plug 7-E, and is drawn through suction tube 39, into the vacuum container 25. The vacuum attachment 21 is connected to a conventional vacuum cleaner hose 34, or the vacuum pump 8 (shown in FIG. 8). The vacuum attachment 21 is connected to the vacuum lid 9 by the vacuum tube 38. The suction creates a vacuum in container 25 pulling the fluid down through suction tube 39 and nose plug 7-E. Sinus congestion is also pulled along with the saline. When half of the saline in container 26 is gone, the wing clips 2 should be rotated, the adjuster plate 5 can then be picked up and rotated one half turn and locked back in the recess 32 (see FIG. 2). This will reverse the nose plugs 7-E and 7-F. Thereby pulling the congestion from the opposing sinuses. A commercially obtained drip tray 37 (shown in FIG. 10) is placed between the two containers 25 and 26. The air compressor 24 has an off on switch 23 within reach of the right hand. By leaning over and placing the nostrils over the nose plugs 7-E and 7-F, both hands are free to operate the system. The pressure container 26 should not be filled more than half full. This will prevent the vacuum container 25 from filling more than half full, thus preventing fluid from entering the vacuum tube 38. After passing through lid 9, tube 38 has two vent holes 35 in the side walls, with a plug 36 in its termination. This helps prevent fluid from entering the vacuum tube 38, and being drawn into the vacuum cleaner hose 34.

Figure 10:
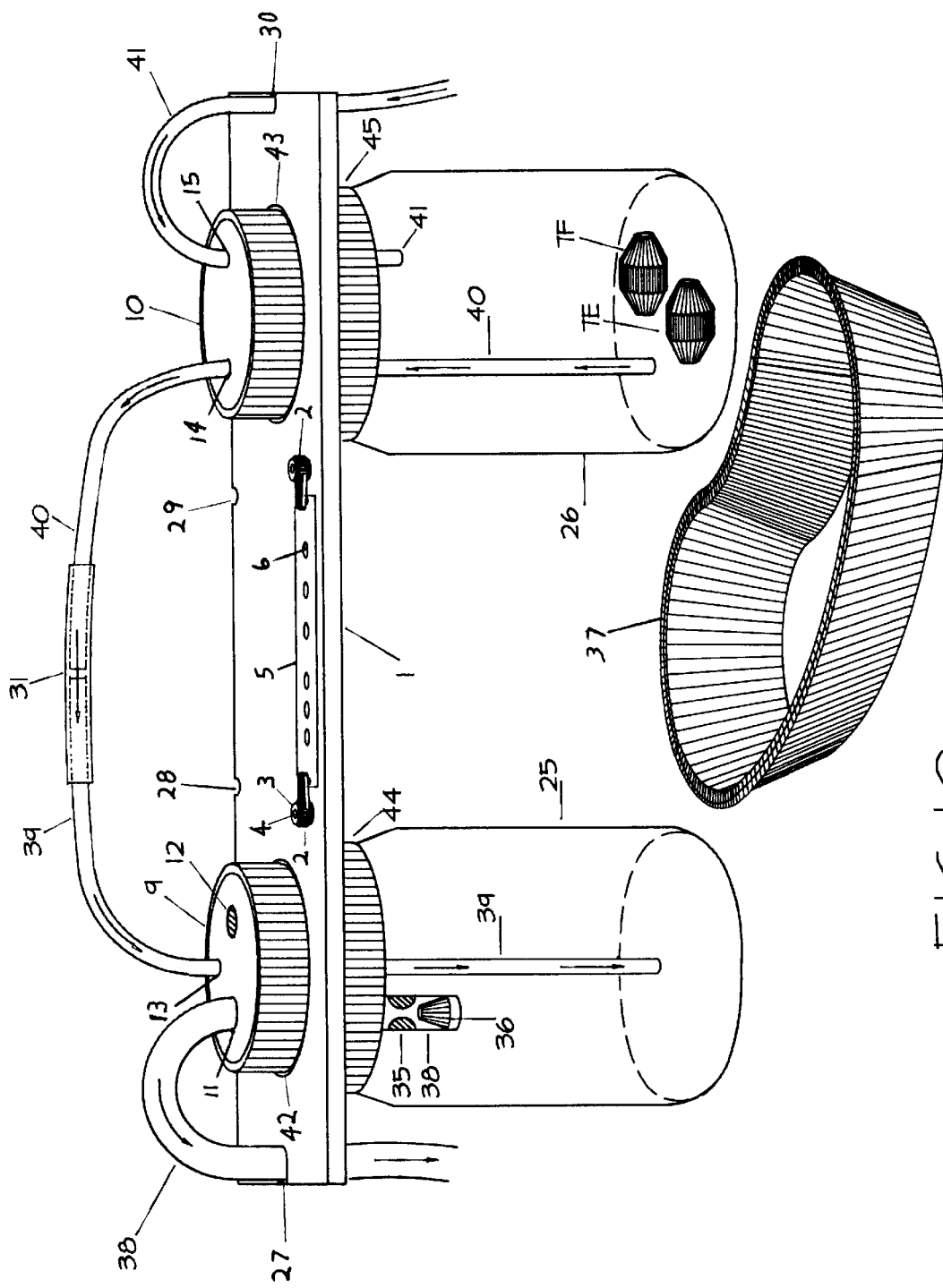
FIG. 10 Shows position of everything to disinfect the nose plugs 7-E and 7-F, suction tube 39 and saline tube 40. A drip tray 37 is shown.

FIG. 10 shows nose plugs 7E and 7F removed from tubes 39 and 40 and placed in the pressure container 26. Pressure container 26 contains 3 oz. of hydrogen peroxide. It should be rinsed around to fully cover the nose plugs, lid 10 should be replaced. Vacuum container 25 should be emptied, rinsed and lid 9 replace . The tubes 39 and 40 are pulled out of adjuster plate 5 and mortise 33 and connected together with the (0.95 cm × 7.62 cm) 3/8"×3" flushing tube 31. The air compressor 24 and vacuum 8 (see FIG. 8) can be turned on. The valve hole 12 is covered with a finger forcing the fluid through tubes 39 and 40. This will disinfect the nose plugs 7E and 7F and tubes 39 and 40. Removing the air compressor 24 (not shown in drawing) from tube 41 and removing the vacuum pump 8 (not shown in drawing) allows the remainder of the system to be put in a dishwasher for sterilization.

While the Sinus Vacuum Flush system has been shown and described in detail, it is obvious that this invention is not to be considered as being limited to the exact form disclosed, and that changes in detail and construction may be made therein within the scope of the invention without departing from the spirit thereof. Accordingly, the scope of the invention should be determined not by the embodiments illustrated, but by the appended claims and their legal equivalents. The invention is defined in the following claims.

I claim:

1. A portable sinus vacuum flush apparatus for dispensing a pressurized fluid medium into the sinus cavities, and for aspirating of material from the sinus cavities, said apparatus comprising:

a rectangle horizontal slab means (1) of suitable material of predetermined size, whereby the slab means accommodates and stabilizes a vacuum container means (25), whereby the container means is held in a large void means (42) in the center of the slab means, whereby the void means communicates with a collar means (44) on the underside of said slab means, whereby said slab means stabilizes and accommodates a pressure container means (26), whereby the container means is held in a large void means (43) in the center of the slab means, whereby the void means (43) communicates with a collar means (45) on the underside of said slab means, whereby said slab means retains multiple easily positioned hollow transport means, whereby the transport means are retained in multiple retainer slot means on said slab means edges, whereby said slab means has a rectangle recess means (32) with a mortise means in the center of a rectangle recess means, whereby the recess means accepts a rectangle adjuster means (5) of suitable material of predetermined size, with a plurality of hole means in the center of a rectangle adjuster means for retaining and adjusting distance between two transport means (39) and (40), whereby the transport means (39) has a nasal seal means (7-E) on its termination, whereby the transport means (40) has a nasal seal means (7-F) on its termination, whereby the adjuster means is removably attached and held in place in said recess means, by multiple rotatably mounted keeper means (2) permanently attached to said slab means at opposing ends of said recess means, whereas said slab means retains said vacuum container means (25) for holding a vacuum to withdraw congestion from the sinus cavities through said nasal seal means (7-E) and said transport means (39), whereby said container means accepts a tight sealing closure means (9) to seal said container means, whereby the closure means further includes a hole means (11) to accept a transport means (38) communicating with a means for creating a vacuum (8), whereby the transport means (38) includes a vacuum attachment means to communicate with said means for creating a vacuum in said container means, whereby said transport means (38) has, on its opposing end on the under side of said closure means, multiple vent hole means (35) on the side of said transport means and an end seal means in its termination, whereby said closure means (9) further includes a valve means (12), whereby said closure means includes a second hole means (13) to accommodate said transport means (39) in communication with said nasal seal means (7-E), whereas said slab means accepts said pressure container means (26) for holding pressure for dispensing a pressurized fluid medium into the sinus cavities through said nasal seal means (7-F) and through said transport means (40), whereby said container means (26) accepts a tight sealing closure means (10) to seal said container means, whereby the closure means includes a hole means (14) to accept said transport means (40) in communication with said nasal seal means (7-F), whereby said closure means (10) further includes a hole means (15) to accept a transport means (41) in communication with a means for creating pressure, and whereby the apparatus further includes a transport means (31) to couple said transport means (39) and said transport means (40) together, for the purpose of flushing a sterile fluid medium to cleanse and disinfect said transport means.

2. The portable sinus vacuum flush apparatus of claim 1 wherein said slab means of predetermined size is a main plate means and is composed of plastic.

3. The portable sinus vacuum flush apparatus of claim 1 wherein said slab means has multiple retainer slot means (27, 28, 29 and 30) of which there are four on the edges of said slab means, to accommodate four said transport means (38, 39,40 and 41).

4. The portable sinus vacuum flush apparatus of claim 1 wherein said transport means are flexible plastic tube means, and are of predetermined size, whereas a vacuum tube means (38) communicates said means for creating a vacuum with said tight sealing closure means (9), whereas the tube means has two said vent hole means and said end seal means in its termination, on the under side of said closure means, whereas said tube means is retained in the slot means (27), whereas a suction tube means (39) communicates with said closure means (9), whereas the tube means travels up through said mortise means in said main plate means, and through the hole means in said adjuster means, to said nasal seal means (7-E), whereas said tube means is retained in the slot means (28), whereas a saline tube means (40) communicates with said closure means (10), whereas the tube means travels up through said mortise means in said slab means, and through said hole means in said adjuster means, to said nasal seal means (7-F), said tube means is retained in the slot means (29), whereas a pressure tube means (41) communicates with said closure means (10), whereas the tube means opposing end communicates with said means for creating pressure, whereas said tube means is retained in the slot means (30), whereas the flushing tube means (31) of larger dimension couples said suction tube means (39), and said saline tube means (40) together, for flushing a sterile fluid medium to cleans and disinfect said tube means.

5. The portable sinus vacuum flush apparatus of claim 1 wherein said slab means has said recess means, with said mortise means in the center thereof, for retaining said adjuster means therein, to accommodate said suction tube means (39) and said saline tube means (40).

6. The portable sinus vacuum flush apparatus of claim 1 wherein said multiple rotatably mounted keeper means includes a pair of plastic wing clip means, wherein the clips means are held in place in two hole means in said slab means with washers and rivets at opposing ends of said recess means.

7. The portable sinus vacuum flush apparatus of claim 1 wherein said adjuster means is a plastic adjuster plate means having a plurality of hole means to stabilize said suction tube means from said vacuum lid means, and said saline tube means from said pressure lid means, and to adjust distance between said nasal seal means.

8. The portable sinus vacuum flush apparatus of claim 7 wherein said adjuster means is removably attached, and secured in said recess means in said slab means by said keeper means, thereby allowing said adjuster means to be removed from said recess means, and rotated one half turn to reverse said saline tube means, and said suction tube means, thereby reversing said nasal seal means mounted on said tube means termination's, to flush and vacuum the opposing sinuses.

9. The portable sinus vacuum flush apparatus of claim 1 wherein said nasal seal means are a pair of plastic nose plug means having a center orifice therein, whereas said seal means are large on one end and small on the opposing end, making them reversible to accommodate different sized nasal openings.

10. The portable sinus vacuum flush apparatus of claim 1 wherein said pressure container means is for holding pressure to deliver a pressurized fluid medium into the nostrils, whereas said container means is composed of glass.

11. The portable sinus vacuum flush apparatus of claim 1 wherein said closure means is a pressure lid means (10) to seal said pressure container means, whereas said closure means is composed of plastic, whereas said closure means has said hole means (15) to accommodate said pressure tube means (41), whereas said closure means has said hole means (14) to accommodate said saline tube means (40), whereas said pressure tube means in communication with said nasal seal means (7-F).

12. The portable sinus vacuum flush apparatus of claim 1 wherein the pressure means is an electric air compressor means to create pressure in said pressure container means, whereby said pressure means further includes an off-on switch means, whereas said pressure tube means (41) is in communication with said pressure means and said pressure lid means, whereas said pressure means is commercially obtained.

13. The portable sinus vacuum flush apparatus of claim 1 wherein said container means for holding a vacuum to withdraw material from the sinuses, whereas said container means is composed of glass.

14. The portable sinus vacuum flush apparatus of claim 1 wherein said closure means is a vacuum lid means (9) to seal said vacuum container means, whereas said closure means is composed of plastic, whereas said closure means has said hole means (11) to accommodate said vacuum tube means (38), whereas said closure means further has said hole means (13), to accommodate said suction tube means (39), whereas the suction tube means is in communication with said nasal seal means (7-E), whereas said closure means has said valve means (12).

15. The portable sinus vacuum flush apparatus of claim 1 wherein the attachment means is composed of plastic and having an opening means (16) to accommodate a conventional vacuum cleaner hose, whereby said attachment means has a mid section means (17) to accommodate a suction regulator hole means (18), and an adjuster sleeve means (20) to partially restrict said suction regulator hole means, whereby said mid section means has a tip means (19) to accept said vacuum tube means (38).

16. The portable sinus vacuum flush apparatus of claim 1 wherein said means for creating a vacuum comprises a vacuum pump, or a conventional vacuum cleaner means.

\* \* \* \* \*